(12) United States Patent
Eastes

(10) Patent No.: US 11,927,548 B2
(45) Date of Patent: Mar. 12, 2024

(54) MECHANICAL COMPONENTS WITH RADIOGRAPHIC MARKERS

(71) Applicant: Science Applications International Corporation, Reston, VA (US)

(72) Inventor: Theodore W. Eastes, Monterey Park, CA (US)

(73) Assignee: Science Applications International Corporation, Reston, VA (US)

( * ) Notice: Subject to any disclaimer, the term of this patent is extended or adjusted under 35 U.S.C. 154(b) by 209 days.

(21) Appl. No.: 17/402,350

(22) Filed: Aug. 13, 2021

(65) Prior Publication Data

US 2023/0048731 A1 Feb. 16, 2023

(51) Int. Cl.
*G01N 23/04* (2018.01)
*G01N 23/083* (2018.01)
*G01N 23/18* (2018.01)

(52) U.S. Cl.
CPC ............. *G01N 23/18* (2013.01); *G01N 23/04* (2013.01); *G01N 23/083* (2013.01)

(58) Field of Classification Search
CPC ....... G01N 23/04; G01N 23/083; G01N 23/18
See application file for complete search history.

(56) References Cited

U.S. PATENT DOCUMENTS

| | | | |
|---|---|---|---|
| 7,998,180 B2 | 8/2011 | Erickson et al. | |
| 9,345,597 B2 | 5/2016 | Pacetti | |
| 9,370,388 B2 | 6/2016 | Globerman et al. | |
| 9,534,889 B2 | 1/2017 | Kim et al. | |
| 9,675,453 B2 | 6/2017 | Guttenberg et al. | |
| 2006/0067465 A1 | 3/2006 | Wilson | |
| 2006/0108545 A1 | 5/2006 | Yoshiki et al. | |
| 2008/0021313 A1 | 1/2008 | Eidenschink et al. | |
| 2009/0022272 A1 | 1/2009 | Joseph et al. | |
| 2010/0091951 A1* | 4/2010 | Ngo | G03B 42/047 378/163 |
| 2015/0314047 A1 | 11/2015 | Lin et al. | |
| 2018/0120246 A1 | 5/2018 | Baucke et al. | |
| 2018/0256231 A1 | 9/2018 | Globerman et al. | |
| 2020/0197121 A1 | 6/2020 | Morey et al. | |
| 2022/0414863 A1* | 12/2022 | Bovero | G06T 7/0008 |

OTHER PUBLICATIONS

Harara, "Digital Radiography in Industry," 17th World Conference on Nondestructive Testing, Oct. 25-28, 2008, Shanghai, China, downloaded Mar. 17, 2021 from <<http://citeseerx.ist.psu.edu/viewdoc/download?doi=10.1.1.216.4675&rep=rep1&type=pdf>>, 6 pages.

Wikipedia entry for "O-ring," downloaded Mar. 28, 2021, <<https://en.wikipedia.org/wiki/O-ring>>, 9 pages.

(Continued)

*Primary Examiner* — Mark R Gaworecki
(74) *Attorney, Agent, or Firm* — Banner & Witcoff, Ltd.

(57) ABSTRACT

Interface surfaces of mechanical system components may comprise one or more radiographic markers. A radiographic marker may comprise a marker material having a radiopacity greater than a radiopacity of a parent material of a mechanical system component that comprises that radiographic marker. Mechanical systems comprising one or more radiographically-marked components may be radiographically imaged to determine wear, damage, and/or other conditions.

20 Claims, 9 Drawing Sheets

(56) References Cited

OTHER PUBLICATIONS

Mc-Master-Cam®, Rotary Shaft Seals, <<https://www.mcmaster.com/seals/dynamic-seals/>>, downloaded Mar. 19, 2021, 22 pages.
Chvartszaid, "Radiographic Journey Through Implant Treatment," Radiographic Journey Through Implant Treatment—Oral Health Group, <<https://www.oralhealthgroup.com/features/radiographic-journey-through-implant-treatment/>>, downloaded Dec. 4, 2020, 9 pages.
Sigakis, et al., "Radiographic Review of Current Therapeutic and Monitoring Devices in the Chest," RadioGraphics, vol. 38, No. 4, <<https://pubs.rsna.org/doi/full/10.1148/rg.2018170096>>, downloaded Dec. 4, 2020, 31 pages.
Hassebrook, "Composite Correlation Filter for O-ring Detection in Stationary Colored Noise," Proc. SPIE 7340, Optical Pattern Recognition XX, 734007 https://doi.org/10.1117/12.819437, downloaded Dec. 4, 2020 from <<https://www.researchgate.net/profile/Laurence_Hassebrook/publication/252804576_Composite_correlation_filter_for_O-ring-detection_in_stationary_colored_Noise/links/544006f60cf2b21758cff777/Composite-correlation-filter-for-O-ring-detection-in-stationary-colored-noise.pdf>>, 8 pages.
U.S. Appl. No. 17/402,339, filed Aug. 13, 2021, titled "Flexible and/or Deformable Mechanical Elements with Radiographic Markers".
Rathi Transpower Private Limited, "Causes of Coupling Failures," prior to Jul. 13, 2021, 6 pages.
"Understanding Diaphragm Failures," priot Jul. 13, 2021, 6 pages.

\* cited by examiner

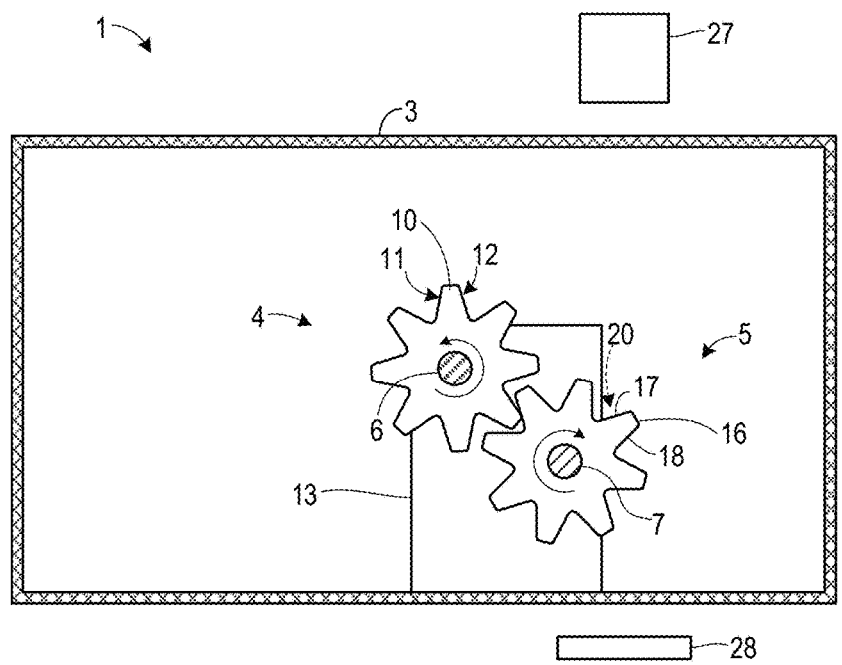
FIG. 3
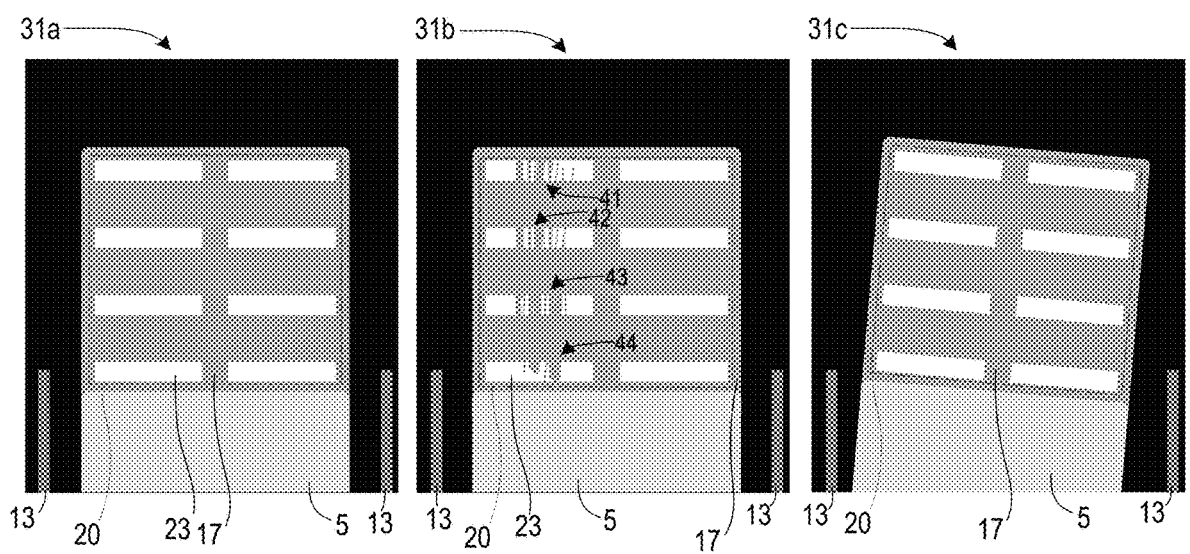
FIG. 4A  FIG. 4B  FIG. 4C

MECHANICAL COMPONENTS WITH RADIOGRAPHIC MARKERS

BACKGROUND

Mechanical assemblies may contain mechanical elements that are subject to wear during their lifetime. However, it is often difficult or impossible to inspect such elements without disassembly or without providing windows or ports through which optical diagnostic devices may be inserted. Disassembly may be time-consuming and/or otherwise inconvenient or impractical. Windows and ports may require significant modifications to the hardware and may provide an entry point for contamination. Moreover, pressure and/or temperature within some mechanical assemblies may impede or prevent use of windows or ports for inspection. Inspection during operation may be beneficial in troubleshooting or in scheduling maintenance.

SUMMARY

This Summary is provided to introduce a selection of some concepts in a simplified form as a prelude to the Detailed Description. This Summary is not intended to identify key or essential features.

Wear and/or other damage to mechanical components (e.g., gear teeth, bearing elements, wheels, cams, cam followers, springs, valve components (e.g., gates, balls, poppets, sleeves, stems, pistons, and seats), brakes, clutches, racks, pistons, piston rings, etc.) having sliding, rolling, impacting, and/or other types of interfaces within a mechanical system may be determined radiographically. Such determination may, for example, be associated with quality inspection, damage inspection, determining installation errors, troubleshooting of operational anomalies, scheduling maintenance, and/or other type of assessment. One or more radiographic markers comprising one or more marker materials may be applied to one or more surfaces of a component (e.g., by mixing into a coating material) to provide information on the condition of the coating and/or of the underlying parent material using radiography, cineradiography, or other radiographic inspection and/or diagnostic methods. The marker material(s) may provide high contrast relative to parent materials of mechanical components of a mechanical system. If a radiographic marker (or portion thereof) is not present in a radiographic image, the wear and/or other damage to an interface surface associated with that marker may be determined. The presence, absence, location, and/or orientation of a radiographic marker in an image may facilitate determining whether one or more components are properly installed, aligned, and/or other than in a desired configuration. Use of radiographic markers may allow inspection of a mechanical system without disassembly and/or while that system is operating.

These and other features are described in more detail below.

BRIEF DESCRIPTION OF THE DRAWINGS

Some features are shown by way of example, and not by way of limitation, in the figures of the accompanying drawings and in which like reference numerals refer to similar elements.

FIG. 3 is a partially schematic diagram showing placement of a radiographic emitter and sensor.

FIGS. 4A, 4B, and 4C are simulated radiographic images of a portion of the system of FIG. 1.

DETAILED DESCRIPTION

Figure 1:
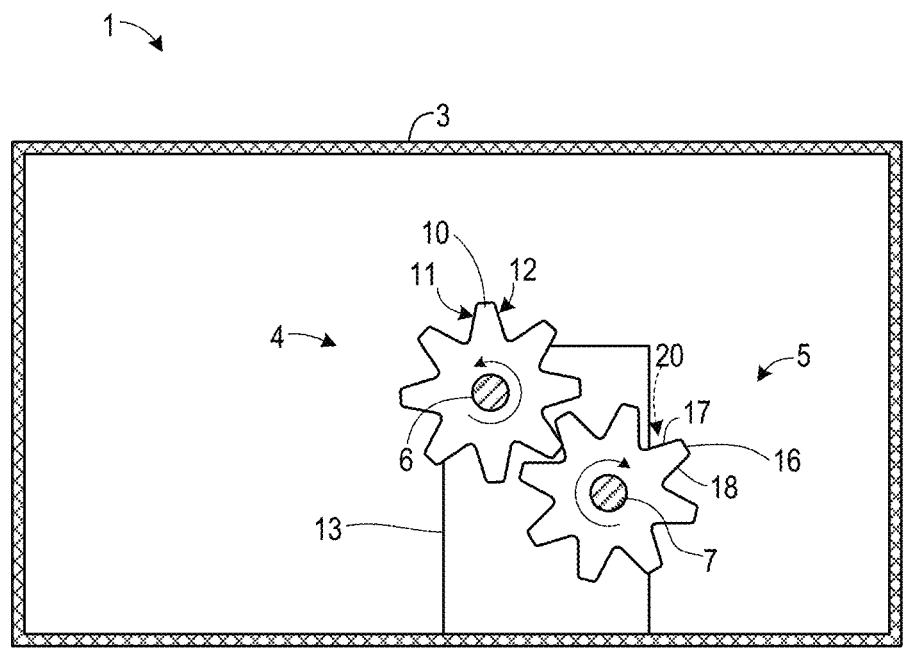
FIG. 1 is a partially-schematic and partially cross-sectional view of an example mechanical system comprising one or more mechanical components with one or more radiographic markers.

A device or other mechanical system may comprise an assembly of one or more mechanical components that may have relative motion and/or interfacing surfaces. For example, an apparatus may comprise components that interact with each other during operation of that apparatus. An interface surface of one of those components may push against (or be pushed against by), support (or be supported by), and/or otherwise contact an interface surface of another of those components as part of the interaction. Contact between interface surfaces may be associated with rolling motion of one or more components, sliding motion of one or more components, percussive (e.g., tapping) motion, and/or other type of motion or combination of types of motions. Numerous non-limiting examples of components configured to have one or more of these types of motion are described herein.

Contact between interface surfaces may result in wear, abrasion, galling, pitting, or other damage to one or more of those surfaces. Interface surfaces may not be easily visible in an assembled mechanical system. For example, those surfaces (and perhaps one or more entire components comprising one or more of those surfaces) may be contained in a housing or other structure that is opaque or translucent to visible light. As another example, interface surfaces and/or entire components may be obscured by other components. Disassembly of a mechanical system to inspect one or more components may be time-consuming and/or otherwise impractical and/or inconvenient, and may preclude inspection of components while the assembled system is operating. Moreover, disassembly may disturb a configuration of components that may be part of a problem (e.g., misaligned or improperly installed components) that an inspection is trying to diagnose.

Using a variety of known techniques, radiographic equipment may be used to inspect assembled parts to assess internal conditions that might otherwise not be visible from an external view of the assembled parts. Such equipment may often, though not exclusively, use x-rays. For example, digital radiographic inspection may comprise positioning an x-ray emitter on one side of an assembly and an x-ray sensor on an opposite side. X-rays from the emitter may pass through the assembly and be detected by pixels of the sensor. Because different materials within the assembly (and/or different thicknesses of materials) may block and/or absorb different amounts of energy from x-rays, data from the pixels may be used to create an image that shows internal details of the assembly. Additional processes such a computed tomography (CT) scanning may be used to combine data from multiple images and/or slices to reveal further internal details.

However, use of radiographic inspection techniques to detect wear, damage, or other conditions of mechanical system components may pose challenges. If a system includes numerous mechanical components, it may be difficult to discriminate individual components or portions thereof in a radiographic image. For example, components may have numerous different shapes and/or may be arranged such that a radiographic image of a region of interest of a particular component requires that x-rays pass through multiple other components (and/or other structures) in addition to the region of interest. The resulting image may be a superimposition of radiographic images of multiple components and/or structures, and discerning the region of interest in that superimposition may be difficult. Moreover, and even if it is possible to obtain a radiographic image that shows a region of interest and that is free of (or at least distinguishable from) superimposed images of other structures, it may not be possible to detect certain types of wear and/or damage. For example, the wear or damage may comprise scratches and/or other type of surface condition that may not be easily detected in some materials and/or at some imaging angles. However, such wear or damage may nonetheless be indicative of a serious problem.

To increase visibility of a mechanical system component (or a portion of a component) during a radiographic inspection, one or more radiographic markers may added to that component. The radiographic marker(s) may be formed from one or more marker materials that absorb x-rays at a higher rate than a parent material of a body of the component and/or at a higher rate than material(s) that form other components of the mechanical system that includes the component. This may allow the radiographic marker(s) to have a higher contrast relative to the component and/or other components. This may help make the marker(s) more visible in a radiographic image and may facilitate inspection of the component without disassembly of a mechanical system. The one or more radiographic markers may be arranged in a pattern. A pattern may, for example, comprise variations in one or more of: presence of one or more marker materials (e.g., one or more regions comprising a marker may be adjacent one or more regions in which a marker is absent), thickness of one or more marker materials (e.g., one or more radiographic markers may be thicker than one or more other radiographic markers), or composition of one or more marker materials (e.g., a marker may comprise one or more portions (e.g., layers, adjacent regions, etc.) formed from different marker materials). A pattern may allow a portion of a mechanical system component to be more easily distinguishable in a radiographic image. For example, the pattern may comprise a collection of shapes, indicia, and or other features that are more likely to be distinguishable from shapes of a component parent material and/or from shapes that may result from superimposition. A pattern may also facilitate detection of wear and/or damage that might otherwise be difficult to visualize, as described more fully below.

For convenience, the characteristic of a material to absorb or otherwise block passage of x-rays (or other radiation used for radiographic imaging) may be referred to as radiopacity. A material with a higher radiopacity will absorb (and/or block) more of such radiation than a material with a lower radiopacity. Radiopacities are known and/or calculable for a wide variety of materials. Radiographic imaging may comprise still imaging, video imaging (e.g., cineradiography), CT, and/or other types of radiographic inspection and/or diagnosis. For example, artificial intelligence may be used (e.g., in combination with known dimensions of components in an imaged system) to deconvolve images that may be superimposed on one another (e.g., to remove portions of an image not needed for diagnosis of a condition of one or more system components).

FIG. 1 is a partially-schematic and partially cross-sectional view of an example mechanical system (e.g., a device or apparatus) 1 that comprises one or more mechanical components, and in which the one or more components may comprise one or more radiographic markers. In FIG. 1 and in subsequent drawing figures, various types of components are shown to provide examples of types of interacting components which may comprise radiographic markers. Other components may be present, but are omitted to simplify explanation and to avoid cluttering drawing figures with unnecessary details. The components shown are not exclusive, and other types of interacting components (e.g., with surfaces interacting via sliding, rolling, percussive, and/or other type motion) may comprise one or more radiographic markers.

The mechanical system 1 comprises a housing 3. The housing 3 is shown in cross-section in FIG. 1, but may completely cover all mechanical components contained therein. The housing 1 may be formed of a material that is opaque and/or translucent to visible light (e.g., light having a wavelength between approximately 400 nanometers (nm) and approximately 750 nm). The components of the mechanical system 1 comprise gears 4 and 5, each of which may be a solid body formed from a parent material (e.g., a metal, a polymer, a composite). The gears 4 and 5 (not shown in cross-section) may rotate about respective shafts 6 and 7 (shown in cross-section). Components of a mechanical system may be moveably coupled to one another so that at least some relative motion is possible, but so that those components are linked in some way (e.g., to constrain movement of those components relative to one another and/or relative to other components). Such movable coupling may be direct and/or indirect. Indirect movable coupling may comprise one or more intervening components that link the movably-coupled components. For example, the gears 4 and 5 may be coupled to one another via the shafts 6 and 7, a bracket 13 located behind the gears 4 and 5, and another bracket 13 (not shown in FIG. 1) in front of the gears 4 and 5. The shafts 6 and 7 may be respectively fixed to the gears 4 and 5, and may be rotatably captured by the brackets 13 (e.g., in pivot holes in the brackets 13).

The gear 4 may comprise a plurality of teeth 10, each having a first face 11 and a second face 12. Similarly the gear 5 may comprise a plurality of teeth 16, each having a first face 17 and a second face 18. When the gears 4 and 5 rotate in the directions indicated in FIG. 1, and assuming the gear 4 is driving the gear 5, the first faces 11 and the first faces 17 may be interface surfaces. As the gears 4 and 5 rotate, each of the first faces 11 contacts one the first faces 17 as their corresponding teeth 10 and 16 engage. The motion of a first face 11 relative to a first face 17 may be a combination of percussive motion (e.g., as a tooth 10 initially engages a tooth 16) and sliding motion (e.g., as a first face 11 slides across the first face 17). If the gear 5 drives the gear 4 in the directions indicated (or if the gear 4 drives the gear 5 in opposite the direction indicated), the second faces 12 and the second faces 18 may be interface surfaces.

Figure 2:
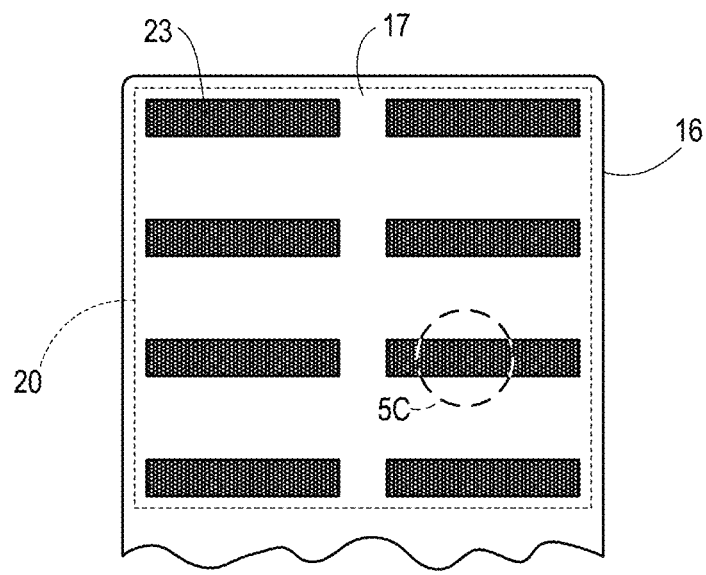
FIG. 2 is a view, of an interface surface of a mechanical component of the system of FIG. 1, showing an example radiographic marker pattern.

At least one of the faces 17 may comprise a pattern 20 of one or more radiographic markers. FIG. 2 is a view of the face 17 of the tooth 16 indicated in FIG. 1 and shows an example configuration of the pattern 20. In the example of FIG. 2, the pattern 20 comprises a collection of eight rectangular radiographic markers 23 arranged in two parallel columns and separated by regions of the face 17 that lack a radiographic marker. The radiographic markers 23, and/or other radiographic markers described herein, may be applied to a surface of the parent material of the tooth 16 and/or otherwise form a portion of the face 17. The radiographic markers 23 may, for example, be applied as a slurry or solution that comprises particles of one or more marker materials having desired radiopacities. Upon drying or curing, the particles or those one or more marker materials may be bonded to the surface of the tooth 16 parent material. Also or alternatively, and depending on the parent material of the tooth 16 (or of another component) and/or the desired marker material, marker materials may be applied by electroplating and/or other process. The thickness of a radiographic marker may be sufficiently thin to avoid interfering with operation of a mechanical component comprising that marker. A radiographic marker may be bonded to a parent material face of a mechanical component directly or indirectly. A directly bonded radiographic marker may comprise one or more marker materials that have been applied directly to a parent material face. An indirectly bonded radiographic marker may comprise one or more marker materials that have been applied to one or more coating materials that have initially been bonded to a parent material face (e.g., the coating material(s) may be bonded directly to the parent material and the marker material(s) may be directly bonded to the coating material(s)). Also or alternatively, a radiographic marker may comprise marker materials that have been added to one or more materials of a coating be applied to a mechanical component for other purposes (e.g., a wear-resistant coating, a corrosion-resistant coating, etc.). A marker material added to such a coating may comprise nanoparticles of the marker material so as to facilitate mixing and/or minimize the effect of the marker material on wear-resisting, corrosion-resisting, and/or other properties of the coating.

Any of various marker materials may be used to form a radiographic marker. Examples include, without limitation, particles and/or nanoparticles of one or more metals (e.g., titanium, tungsten, boron, gold, silver), metal oxides (e.g., titanium dioxide, bismuth oxide, zirconium oxide), and/or other materials (e.g., barium sulfate). The marker material or materials selected for use as a radiographic marker may have radiopacities greater than a radiopacity of the parent material from which a mechanical component (or a portion of that mechanical component comprising the radiographic marker) is formed. Those marker materials may also or alternatively be selected based on an intended end-use of a radiographically-marked mechanical component. If, for example, a mechanical component is formed from a parent material having a lower radiopacity (e.g., certain types of composites and/or plastics) and is to be used in a mechanical system in which a housing and/or other mechanical components are also formed from materials having lower radiopacities, marker material(s) selected for a radiographic marker may have less radiopacity than may be the case for a radiographic marker for a mechanical component formed from a parent material with a higher radiopacity (e.g., certain metals) and/or which is intended for use in a mechanical system comprising mechanical components formed one or materials with higher radiopacities. Also or alternatively, materials with higher radiopacity (e.g., gold, titanium, silver) may be advantageous for use in very thin markers.

FIG. 3 is a partially schematic diagram showing placement of a radiographic emitter 27 and a radiographic sensor 28 for inspection of the face 17 of the mechanical component 5 as installed in the mechanical system 1. The emitter 27 may comprise a source of X-rays or other radiation (e.g., gamma radiation) able to penetrate the material(s) of the mechanical system 1. The sensor 28 may comprise an array of pixels configured to detect incident radiation and determine an intensity of such radiation, and to output signal data that may be used (e.g., by image processing software executing on a computing device) to generate a radiographic image. Radiographic emitters and sensors, as well as other equipment used to generate radiographic images and perform radiographic inspection, are well known and thus not further described herein.

FIG. 4A is an example simulated radiographic image 31*a*, associated with the placement of the emitter 27 and the sensor 28 shown in FIG. 3, of a portion of the mechanical system 1. In the example of the image 31*a*, the portion of the mechanical component 5 near the bottom is lighter because of the presence of more parent material in that region. Portions of the brackets 13 are also visible. The radiographic markers 23 of the pattern 20 have a brighter appearance because of a higher radiopacity of the marker material(s) of the markers 23. In the simulated image 4A, the radiographic markers 23 are intact, thereby indicating an absence of wear or damage. The location and/or orientation of the radiographic markers 23 within the image 4A may be indicative of whether the mechanical component 5 has been properly installed. A complete or partial absence of one or more radiographic markers may indicate, for example, that a surface associated with the absent marker(s) has been worn or otherwise damaged.

An example of this is shown in FIG. 4B, which is another example simulated radiographic image 31*b*, associated with the placement of the emitter 27 and the sensor 28 shown in FIG. 3, of the same portion of the mechanical system 1. In example of the image 31*b*, portions of some radiographic markers 23 have been worn away and/or otherwise removed, resulting in regions 41, 42, 43, and 44 appearing in the image 31*b*. The condition of the face 17 shown by the image 31*b* may be indicative of uneven wear, misalignment, and/or other problems.

FIG. 4C is a further example simulated radiographic image 31*c*, associated with the placement of the emitter 27 and the sensor 28 shown in FIG. 3, of the same portion of the mechanical system 1. In the example of the image 31*c*, pattern 20 of the radiographic markers 23 is angled to one side of the image. The orientation of the face 17 shown by the image 31*c* may be indicative of misalignment, improper installation, and/or other problems.

Multiple surfaces of a mechanical component, and/or of multiple mechanical components of a mechanical system, may comprise one or more patterns of one or more radiographic markers. For example, in the mechanical system 1, faces 17 of multiple teeth 17 may comprise the pattern 23 and/or another pattern. Also or alternatively, the pattern 23 (and/or another pattern) may be included on one or more faces 11 of one or more teeth 10, on one or more faces 12 of one or more teeth 10, and/or on one or more faces 18 of one or more teeth 16

To avoid interference in a radiographic image from superimposition (e.g., from radiographic markers on the top and bottom faces of an element being imaged along an x-ray path passing through both faces), radiographic markers may be omitted from one or more surfaces of one or more mechanical components. For example, radiographic markers may be omitted from the face 18 of a tooth 16 having radiographic markers on its face 17. If radiographic marking of faces 17 and 18 are desired, radiographic markers may be provided on a face 17 of one tooth 16 and absent from the face 18 of that tooth 16, with radiographic markers provided on a face 18 of a different tooth 16 and absent from the face 17 of that different tooth 16. In some cases, superimposition-related interference of markers on different faces may be avoided by using different patterns of radiographic markers on those different faces. For example, a top face of a mechanical component may comprise radiographic markers in a "+" pattern, and a bottom face of that mechanical component may comprise radiographic markers in a pattern of four squares located in regions that would fit within open spaces of the "+" pattern.

Figure 5A:
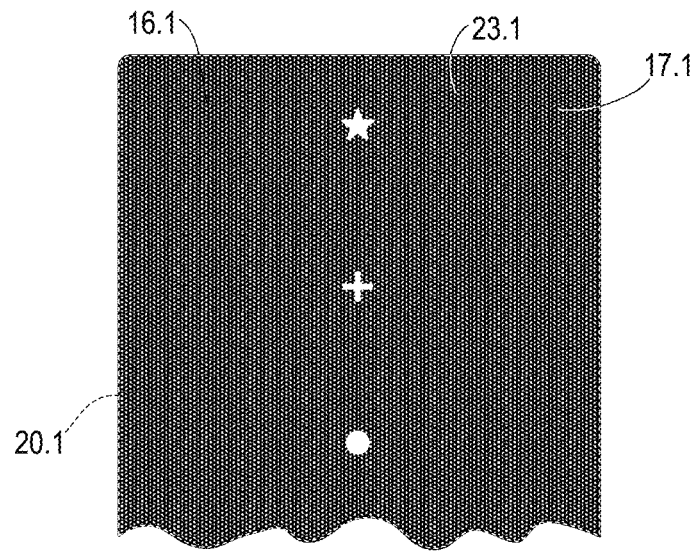
FIGS. 5A and 5B show additional examples of radiographic marker patterns.
Figure 5B:
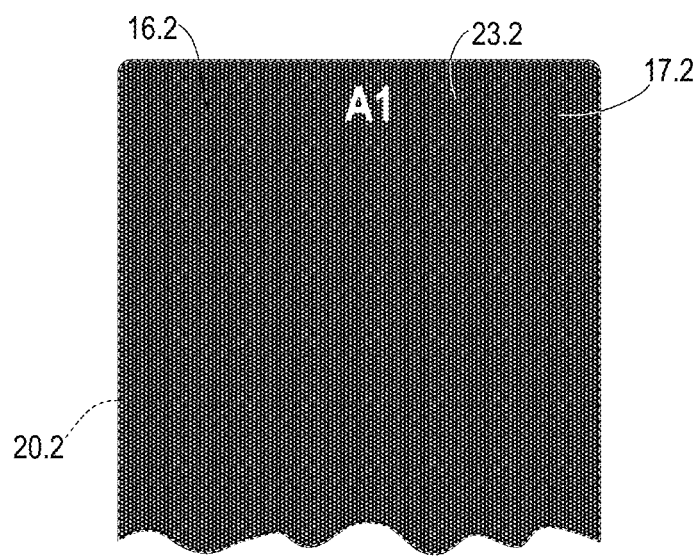

A pattern may comprise any configuration of one or more radiographic markers. FIGS. 5A and 5B show examples of patterns that may comprise a single radiographic marker that surrounds one or more regions in which a marker material may be absent. The region(s) lacking marker material may have a shape that corresponds to one or more types of indicia (e.g., characters such as letters and/or numbers, symbols).

FIG. 5A shows a face of a tooth 17.1 of a gear tooth 16.1 that may be similar to the face 17 of the tooth 16. In the example of FIG. 5A, however, a pattern 20.1 comprises a radiographic marker 23.1 covering substantially all of the face 17.1. Portions of the pattern 20.1 omit marker material in a region having a shape of a star symbol, in a region having a shape of a "+" symbol, and in a region having a shape of a circle symbol. In a radiographic image, these three symbols may be used to identify the radiographic marker 23.1 and may help distinguish it from images of surrounding structure.

FIG. 5B shows a face of a tooth 17.2 of a gear tooth 16.2 that may be similar to the face 17 of the tooth 16. In the example of FIG. 5B, and similar to FIG. 5A, a pattern 20.2 comprises a radiographic marker 23.2 covering substantially all of the face 17.2. In the example of FIG. 5B, however, portions of the pattern 20.2 omit marker material in regions having shapes of characters ("A1"). In a radiographic image, these characters may be used to identify the face 17.2 and to distinguish it from similar faces of one or more other teeth 16.2 that have similar patterns, but with different indicia. For example, a face 17.2 on a tooth 16.2 on an opposite side of a gear may have a pattern similar to the pattern 20.2, but with a marker that omits marker material in regions having shapes of the characters "A2". Seeing "A1" or "A2" in the image may allow determination of a rotational position of that gear.

A pattern of one or more radiographic markers need not comprise indicia. For example, a pattern may comprise a single radiographic marker such as the radiographic marker 23.1 or the radiographic marker 23.2, but without any of the marker material (or materials) removed to create indicia. A pattern may comprise a variation in thickness of marker material(s), a variation in marker material(s), or other variations. A radiographic marker may cover an entire surface.

A radiographic marker may be formed from a single marker material. Alternatively, a radiographic marker may comprise multiple marker materials. For example, a radiographic marker may comprise layers of different marker materials having different opacities. At least some such layers may be used to determine an extent of wear or other damage. For example, marker material opacities may decrease from outer layers to inner layers. As a radiographically-marked interface surface is contacted by another interface surface, the outer layers of marker material may be the first to be scratched, eroded, and/or otherwise removed (in whole or in part), followed by inner layers. If the opacity of an eroded outer layer is greater than an opacity of an underlying layer, and as explained in more detail below, the overall opacity of the radiographic marker may be reduced in the region of erosion. As more of the radiographic marker is eroded, the overall opacity of the radiographic marker may be further reduced.

Figure 5C:
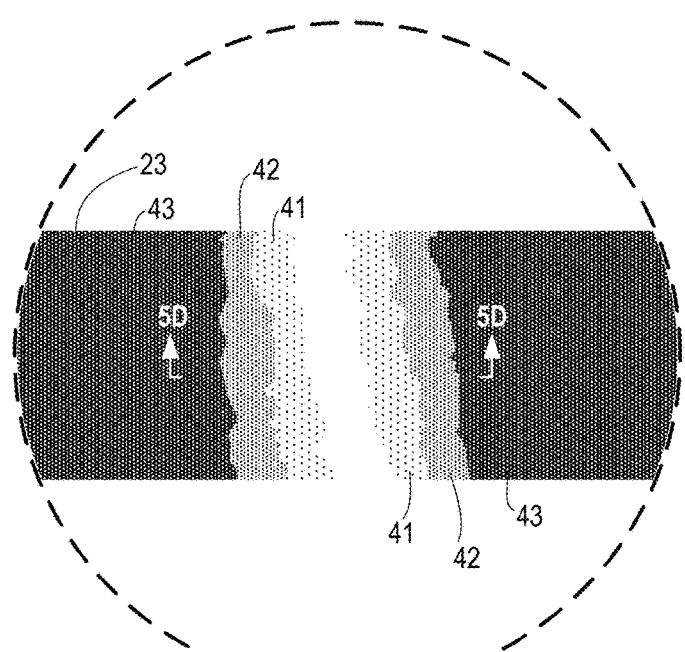
FIG. 5C is an enlarged view of a portion of a radiographic marker, from the region indicated in FIG. 2, after wear or other damage.
Figure 5D:
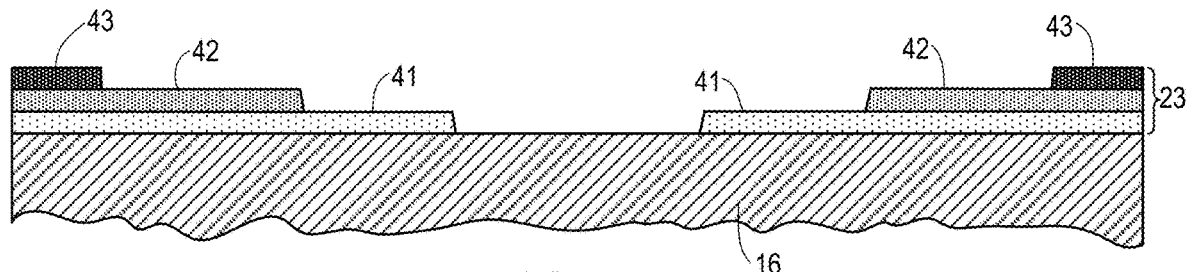
FIG. 5D is a further enlarged area cross-sectional view from the location indicated in FIG. 5C.

FIG. 5C is an enlarged view, from the region indicated in FIG. 2, of one of the radiographic markers 23 after wear or other interaction has caused portions of that radiographic marker 23 to be eroded. FIG. 5D is a further enlarged area cross-sectional view from the location indicated in FIG. 5C. As shown in FIGS. 5C and 5D, the radiographic marker 23 may comprise 3 layers 41, 42, and 43. The layer 41 may be an innermost layer (e.g., closest to the parent material of the tooth 16) and may be formed from a first marker material. The layer 42 may be an intermediate layer and may be formed from a second marker material. The layer 43 may be an outermost layer (e.g., furthest away from the parent material of the tooth 16) and may be formed from a third marker material. The radiopacity of the third marker material of the layer 43 may be greater than the radiopacity of the second marker of the layer 42. The radiopacity of the second marker material of the layer 42 may be greater than the radiopacity of the first marker of the layer 41. The radiopacity of the first marker material of the layer 41 may be greater than the radiopacity of the parent material of the tooth 16.

Figure 5E:
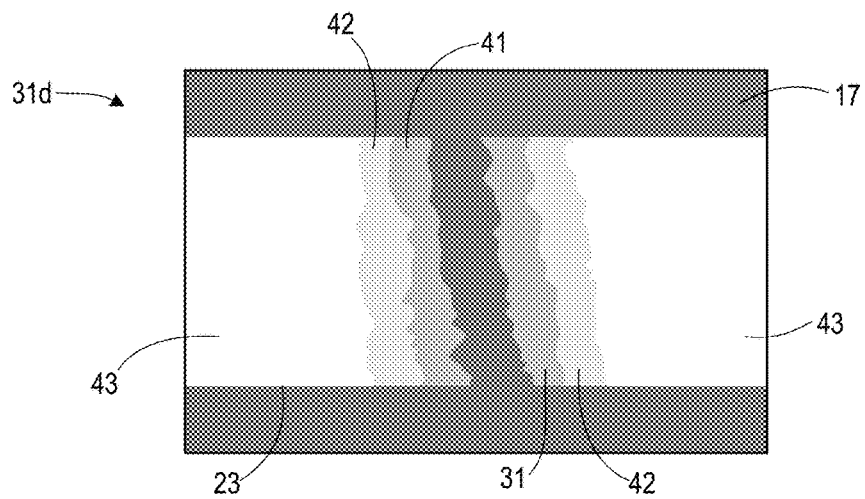
FIG. 5E is a simulated radiographic image of the portion of the radiographic marker of FIG. 5C.

FIG. 5E is a simulated radiographic image of the portion of the radiographic marker 23 as shown in FIG. 5C. Because the radiopacity of the third marker material of the layer 43 is higher than the radiopacities of the respective second and first marker materials of the layers 42 and 41, the layer 43 prevents appearance of the layers 42 and 41. However, and as seen by comparing FIG. 5E with FIGS. 5C and 5D, removal of a portion of the layer 43 allows a portion of the layer 42 to appear. Similarly, removal of a portion of the layer 42 allows a portion of the layer 41 to appear, and removal of a portion of the layer 41 allows the appearance of a portion of the tooth 16 parent material previously covered by the eroded portion of the layer 41. A radiographic marker could comprise more layers, and the radiopacities of the materials of those layers may decrease for layers that are further from an outer layer. A radiographic marker could comprise fewer layers.

Figure 6A:
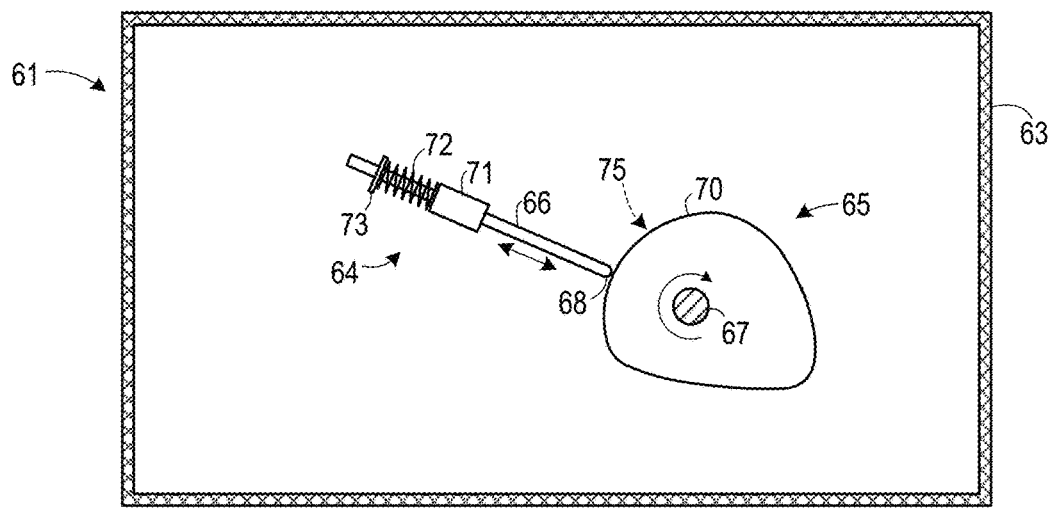
FIGS. 6A, 6B, 6C, and 6D are partially-schematic and at least partially cross-sectional views of example mechanical systems comprising mechanical components having interface surfaces that slide relative to one another and that comprise one or more radiographic markers.

The mechanical system 1 and the gears 4 and 5 shown in FIG. 1 are merely one example of a mechanical system and mechanical components that may comprise radiographic markers. FIGS. 6A, 6B, 6C, and 6D are partially-schematic and at least partially cross-sectional views of additional non-limiting example mechanical systems comprising mechanical components having interface surfaces that slide relative to one another and that comprise one or more radiographic markers. FIG. 6A shows a mechanical system 61 that may comprise a housing 63 (which may be similar to the housing 3). The components of the system 61 comprise a cam 65 and a cam follower 64. The cam 65 may rotate in the direction indicated about an shaft 67. The cam follower 64 comprises a rod 66 that may move back and forth in the direction indicated as a tip 68 of the rod 66 follows a cam profile surface 70 of the cam 65. The rod 66 may be supported by a sleeve bearing 71 and may be kept in contact with the cam 65 by a spring 72 extending between the sleeve bearing 71 and a flange 73 fixed to the rod 66. In FIG. 6A, only the housing 63 and the shaft 67 are shown in cross-section. The mechanical system 63 may comprise additional components (e.g., one or more components supporting and/or movably coupling the shaft 67 and/or the sleeve bearing 71, one or more components acted upon by the rod 66, one or more components causing rotation of the shaft 67, etc.). The cam profile surface 70 may be an interface surface subject to sliding motion contact of the tip 68. Some or all of the surface 70 and may comprise a pattern 75 of one or more radiographic markers to facilitate radiographic inspection of the cam 65. Also or alternatively, the tip 68, other portions of the rod 66, other portions of the cam 65, and/or other components and/or component portions may comprise a pattern of one or more radiographic markers to facilitate radiographic inspection.

Figure 6B:
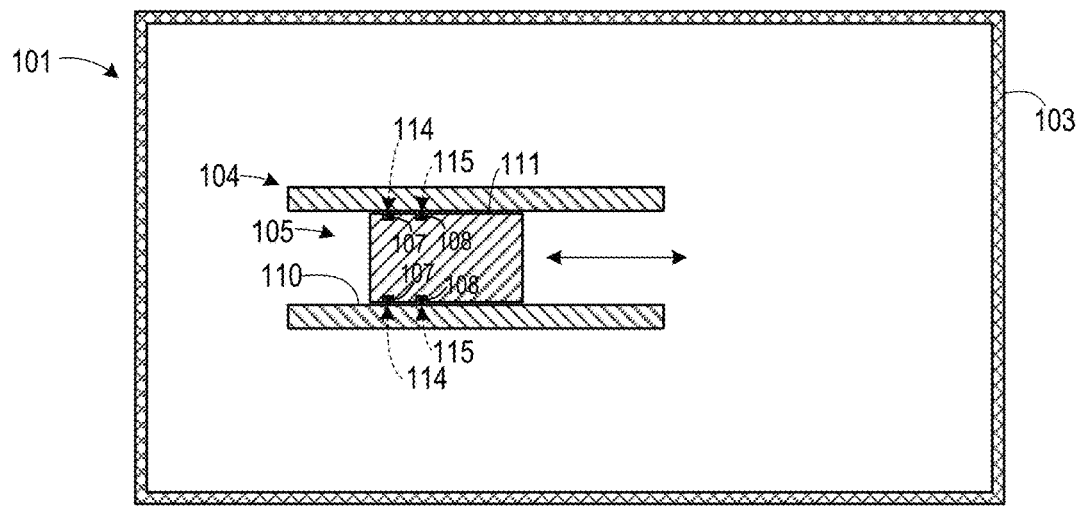

FIG. 6B shows a mechanical system 101 that may comprise a housing 103 (which may be similar to the housing 3). The housing 103 and other components are shown in cross-section. The components of the system 101 comprise a piston 105 that moves in the directions indicated within a cylinder 104. The piston 105 may comprise rings 107 and 108 that contact (and slide against) an inner wall 110 of the cylinder 104, and/or an outer surface 111 of the piston 105 may contact (and slide against) inner wall 110 of the cylinder 104. The mechanical system 101 may comprise additional components (e.g., one or more components supporting and/or movably coupling the cylinder 104 and/or the piston 105, one or more components acting on or acted upon by the piston 105, etc.). Any of the outer surfaces of the rings 107 and 108, the inner wall 110, and/or the outer surface 111 may be an interface surface and may comprise a pattern of one or more radiographic markers to facilitate radiographic inspection. For example, the outer surfaces of the rings 107 and 108 may comprise patterns 114 and 115.

Figure 6C:
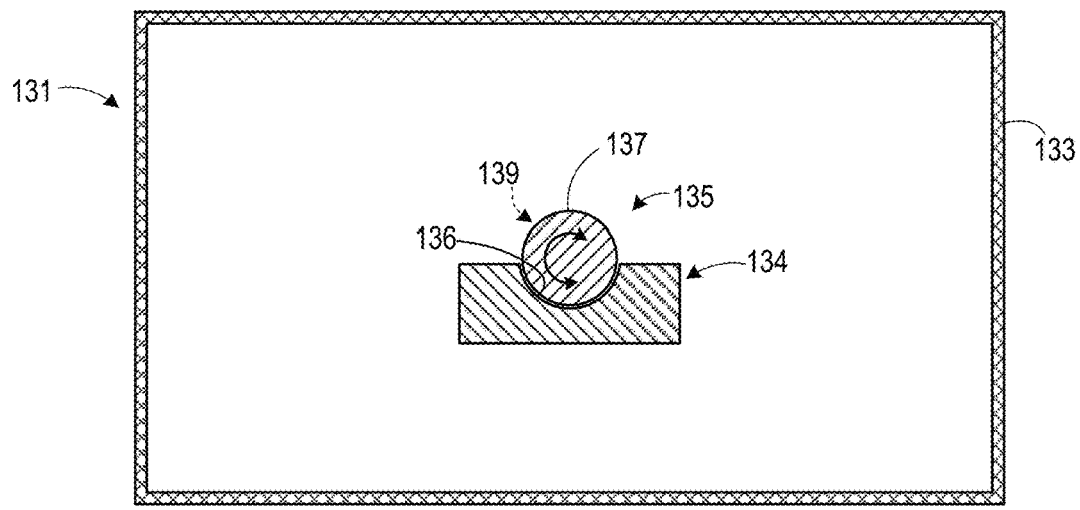

FIG. 6C shows a mechanical system 131 that may comprise a housing 133 (which may be similar to the housing 3). The housing 133 and other components are shown in cross-section. The components of the system 131 comprise a journal 135 that is supported by a journal bearing 134 and that may rotate in the directions indicated. An outer surface 137 of the journal 135 may contact (and slide against) bearing surface 136 of the journal bearing 134. The mechanical system 131 may comprise additional components (e.g., one or more components supporting and/or movably coupling the journal 135 and/or the journal bearing 134, one or more components acting on or acted upon by the journal 135, etc.). The outer surface 137 and/or the bearing surface 136 may be an interface surface and may comprise a pattern of one or more radiographic markers to facilitate radiographic inspection. For example, the outer surface 135 may comprise a pattern 139.

Figure 6D:
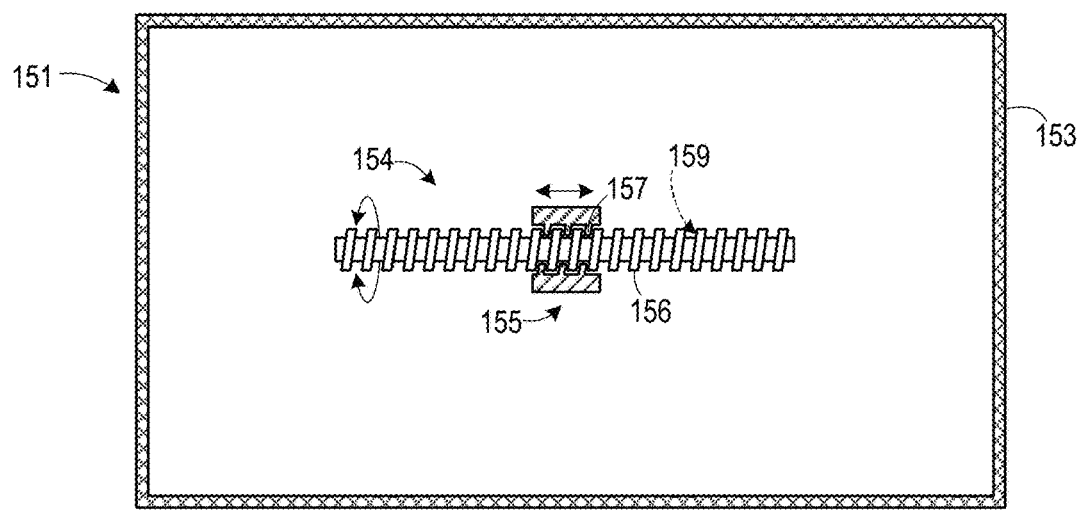

FIG. 6D shows a mechanical system 151 that may comprise a housing 153 (which may be similar to the housing 3). The components of the system 151 comprise a screw 154 and a nut 155. The housing 153 and the nut 155 are shown in cross-section. Threads 156 of the screw 154 may interact with internal threads 157 of the nut 155 to advance the nut 155 as the screw 154 is rotated. Side surfaces of the screw threads 156 may contact (and slide against) side surfaces of the threads 157. The mechanical system 151 may comprise additional components (e.g., one or more components supporting and/or movably coupling the screw 154 and/or the nut 155, one or more components acting on or acted upon by the nut 155 and/or the screw 154, etc.). The side surfaces of the screw threads 156 and/or the side surfaces of the threads 157 may be interface surfaces and may comprise patterns of one or more radiographic markers to facilitate radiographic inspection. For example, a side surface of the threads 156 may comprise a pattern 159.

Figure 7A:
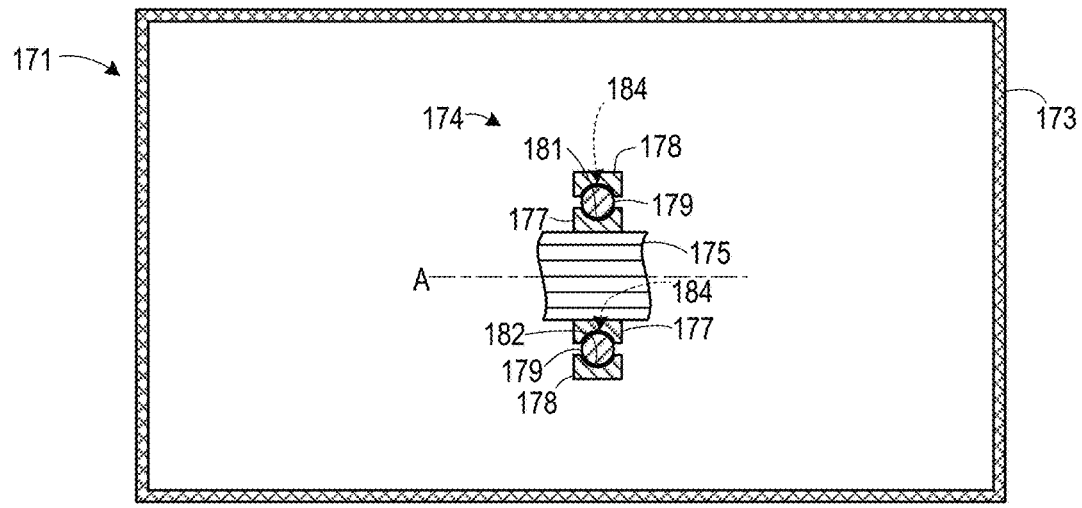
FIGS. 7A and 7B are partially-schematic and at least partially cross-sectional views of example mechanical systems comprising mechanical components having interface surfaces that roll relative to one another and that comprise one or more radiographic markers.
Figure 7B:
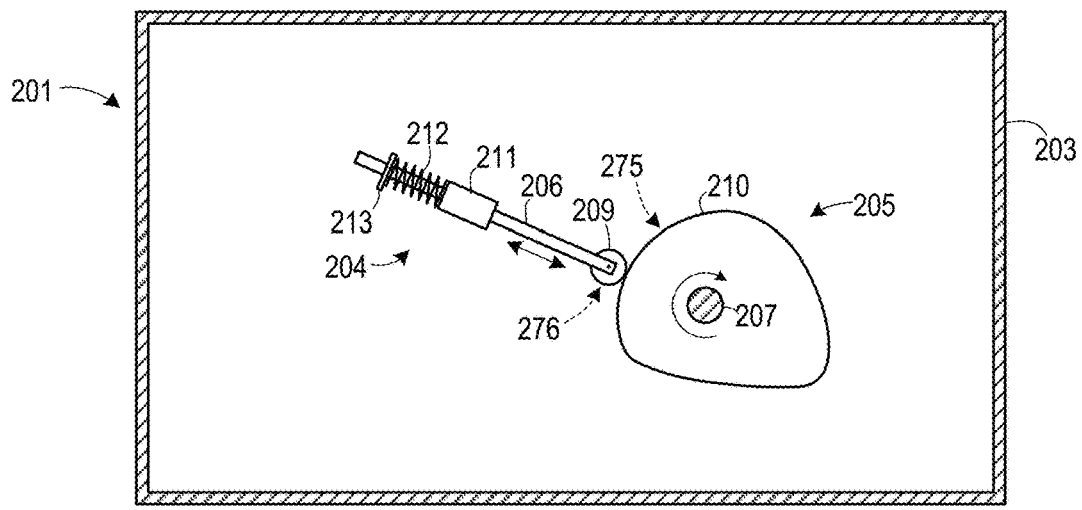

FIGS. 7A and 7B are partially-schematic and at least partially cross-sectional views of example mechanical systems comprising mechanical components having interface surfaces that roll relative to one another and that comprise one or more radiographic markers. FIG. 7A shows a mechanical system 171 that may comprise a housing 173 (which may be similar to the housing 3). The housing 173 and other components are shown in cross-section. The components of the system 171 comprise a bearing assembly 174 supporting a shaft 175 for rotation about an axis A. The bearing assembly 174 may comprise an inner race 177, an outer race 178, and ball bearings 179. Also or alternatively, the bearing assembly 174 may comprise roller bearings and/or bearings having other shapes. The inner race 177 may be fixed to the shaft 175 and the outer race 178 may be separately supported by other structure (not shown). As the shaft inner race 177 rotates with the shaft 175, the surfaces of the ball bearings 179 roll over the surface 181 of the inner race 177 and the surface 182 of the outer race 178. The mechanical system 171 may comprise additional components (e.g., one or more components supporting the shaft 175 and/or the bearing assembly 174, one or more components acting on or acted upon by the shaft 175 and/or the bearing assembly 174, etc.). The surfaces of the ball bearings 179, the surface 181, and/or the surface 182 may be interface surfaces and may comprise patterns of one or more radiographic markers to facilitate radiographic inspection. For example, surfaces of the ball bearings may comprise a pattern 184.

FIG. 7B shows a mechanical system 201 that may comprises a housing 203 (which may be similar to the housing 3). The system 201 may be similar to the system 61, and may comprise a cam follower 204, cam 205, rod 206, shaft 207, cam profile surface 210, sleeve bearing 211, spring 212, and flange 213 that may respectively be similar to the cam follower 64, the cam 65, the rod 66, the shaft 77, the cam profile surface 70, the sleeve bearing 71, the spring 72, and the flange 73. Unlike the rod 66, however, an end of the rod 206 comprises a rotatably mounted follower wheel 209 and that has an outer surface that contacts (and rolls along) the cam profile surface 210. The outer surface of the follower wheel 209 and/or the cam profile surface 210 may be interface surfaces and may comprise patterns of one or more radiographic markers to facilitate radiographic inspection. For example, some or all of the cam profile surface 210 may comprise a pattern 275 and/or some or all of the outer surface of the follower wheel 209 may comprise a pattern 276.

Figure 7C:
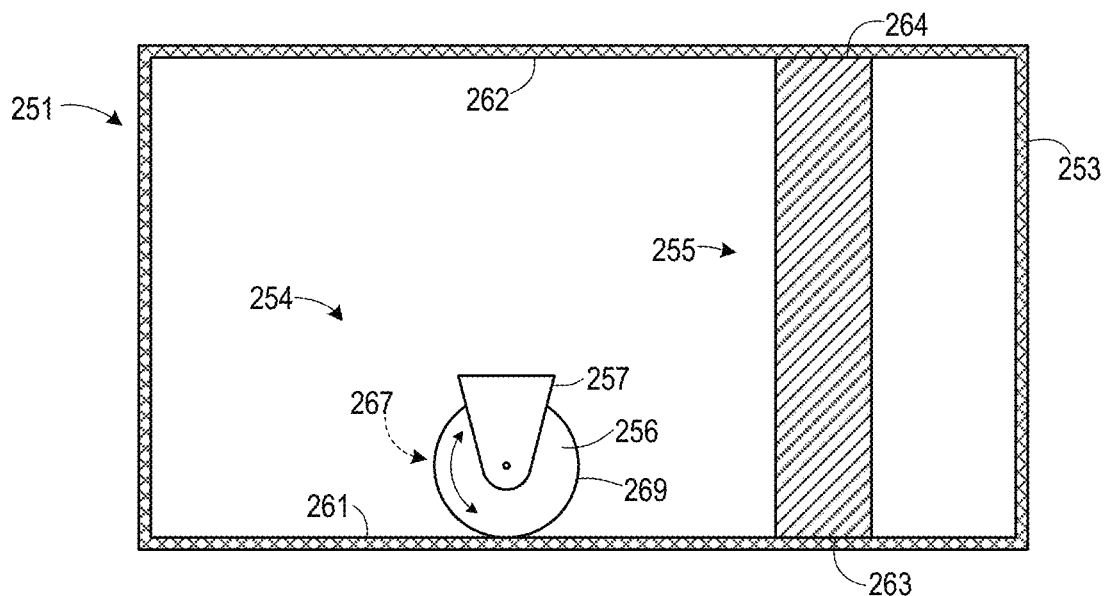
FIG. 7C is a partially-schematic and partially cross-sectional view of another example mechanical system comprising mechanical components having interfaces that slide or roll relative to one another and that comprise one or more radiographic markers.

A housing may be a component of a mechanical system having one or more interface surfaces that interact with one or more interface surfaces of one or more other mechanical components of the system. Several examples are shown in FIG. 7C, a partially-schematic and partially cross-sectional view of an example mechanical system 251 comprising a housing 253 (which may be similar to the housing 3). Components of the system 251, in addition to the housing 253, comprise a wheel assembly 254 and a plate 255. The wheel assembly 254 may comprise a wheel 256 that is rotatably mounted to a bracket 257 and that has a wheel outer surface 269. As the wheel 256 rotates in one of the directions shown, the surface 269 may contact (and roll against) an inner surface 261 of the housing 253. The plate 255 may comprise a lower surface 263 and an upper surface 264 that respectively contact (and slide against) the inner surface 261 and another inner surface 262 of the housing 253. The sliding of the plate surfaces 263 and 264 against the inner surface 261 and 262 may occur as the plate 255 may moves linearly (e.g., if the plate 255 is a movable bulkhead) or rotationally (e.g., if the plate 255 is a valve plate). The mechanical system 251 may comprise additional components (e.g., one or more components supporting, acting on, and/or acting against the bracket 257; one or more components acting on and/or acting against the plate 255; etc.). Also or alternatively, the plate 255 or the wheel assembly 254 may be omitted. The surface 269, the inner surface 261, the inner surface 262, the surface 263, and/or the surface 264 may be interface surfaces and may comprise patterns of one or more radiographic markers to facilitate radiographic inspection. For example, the surface 269 may comprise a pattern 267.

Radiographic markers may be used in connection with any type of mechanical component. Although various non-limiting examples are described above and shown in the drawings, there are numerous types of components to which radiographic markers may added so as to facilitate radiographic inspection of such components in a mechanical system. Additional non-limiting examples include rails and or other guides, components that move along rails and/or other guides, hinges, latches, springs, valve seats, brakes, clutches, racks, pinions, worm gears, other types of gears, pulleys, edges of hatches and/or hatch openings, detents, clevises and/or clevis pins, drive chains, universal joints, constant velocity joints, stops, pawls, ratchets, linkages, etc.

Figure 8:
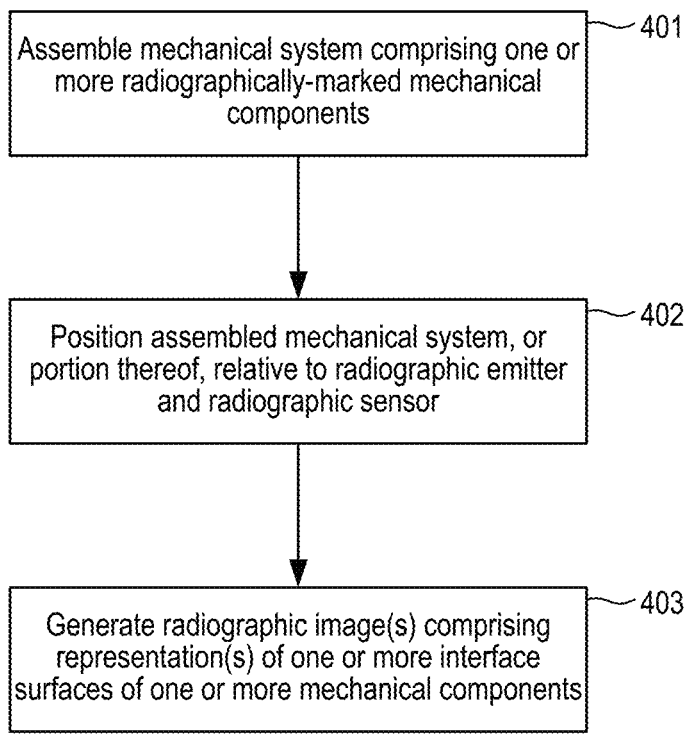
FIG. 8 is a flow chart showing an example method for radiographic inspection of a mechanical system in which one or more interacting mechanical components comprise one or more radiographic markers.

FIG. 8 is a flow chart showing steps of an example method for radiographic inspection of a mechanical system incorporating one or more mechanical components having at least one interface surface that comprises one or more radiographic markers (e.g., a pattern of one or more radiographic markers). One or more steps of the method may be omitted, performed in an order other than shown in FIG. 8, and/or otherwise modified. One or more other steps may be added.

In step 401, a mechanical system comprising one or more radiographically-marked mechanical components (e.g., one or more of the components described herein comprising one or more interface surfaces having one or more radiographic markers (e.g., a pattern of one or more radiographic markers) such as described herein) may be assembled. For example, components, such as those shown in one or more of FIG. 1, 3, or 6A-7C, and/or other components, may be assembled within a housing.

In step 402, the assembled mechanical system, or a portion thereof, may be positioned relative to a radiographic emitter (e.g., the emitter 27) and a radiographic sensor (e.g., the sensor 28). The positioning of step 402 may comprise placing the emitter and/or sensor relative to the structure (or portion thereof) and/or placing the structure (or portion thereof) relative to the emitter and/or sensor. The positioning may comprise positioning the mechanical system so that at least a first radiographically-marked interface surface of at least a first component is positioned between the emitter and the sensor.

In step 403, one or more radiographic images may be generated based on detection, by the sensor, of radiographic energy emitted by the emitter. The radiographic energy may be emitted while the mechanical system is operating (e.g., while at least the first radiographically-marked interface surface is undergoing contacting motion relative to a second interface surface of a second mechanical component that is movably coupled to the first mechanical component). The one or more generated images (e.g., images such as the simulated images 31a, 31b, 31c, and/or 31d) may comprise one or more images of the first interface surface and/or of one or more other interface surfaces. The representation(s) may comprise representations of the one or more radiographic markers (or an absence of one or more radiographic markers or one or more portions thereof) and may indicate a condition of the first interface surface and/or of the first mechanical component.

A radiographic marker need not extend uniformly throughout a coating or coating layer. For example, a coating may comprise a layer in which a first coating material forms a portion of that layer and a second coating material forms another portion of that layer. The first coating material may have a radiopacity that is less than (or greater than) a radiopacity of the second coating material. For example, the second coating material may be similar to the first coating material, but may further comprise particles (e.g., nanoparticles) of a marker material that cause the second coating material to have a radiopacity greater than a radiopacity of the first coating material. A coating layer having regions formed from different coating materials may, for example, be formed by inkjet printing.

FIGS. 9A through 9E show examples of coating material layers that comprise different coating materials. As explained below, such layers may be used for wear detection.

Figure 9A:
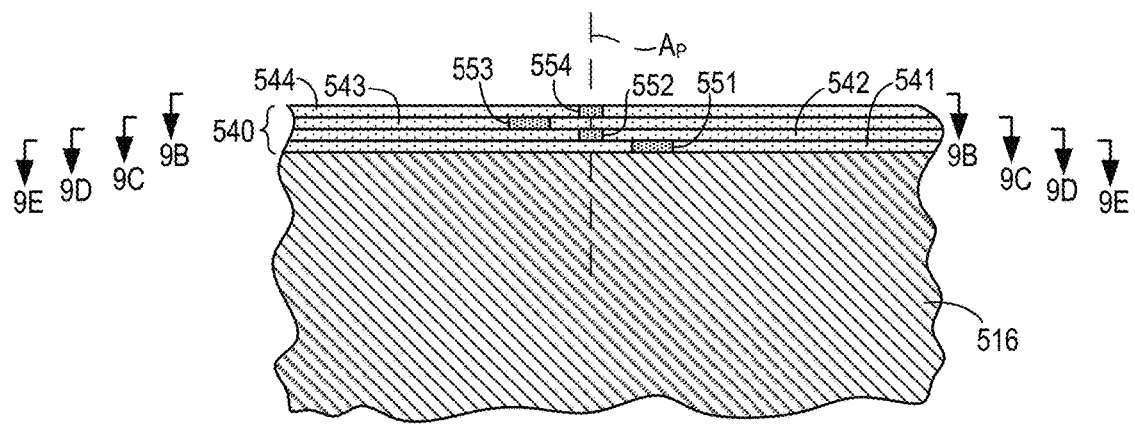
FIG. 9A is a partially schematic area cross-sectional view of an example multilayer coating, comprising a plurality of radiographic markers, forming at least a portion of an interface surface of a mechanical component.

FIG. 9A is a partially schematic area cross-sectional view of an example multilayer coating 540, comprising a plurality of radiographic markers, forming at least a portion of an interface surface of a mechanical component 516. The component 516 may be a gear tooth, a wheel or other rolling element, a surface over which a wheel or other element rolls or slides, and/or any other type of mechanical component. The coating 540 comprises a layer 541 applied to a surface of the component 516, a layer 542 applied to the layer 541, a layer 543 applied to the layer 543, and a layer 544 applied to the layer 543. A region of the layer 541, formed from a material having a radiopacity higher than a radiopacity of a material forming other parts of the layer 541, defines a radiographic marker 551. A region of the layer 542, formed from a material having a radiopacity higher than a radiopacity of a material forming other parts of the layer 542, defines a radiographic marker 552. A region of the layer 543, formed from a material having a radiopacity higher than a radiopacity of a material forming other parts of the layer 543, defines a radiographic marker 553. A region of the layer 544, formed from a material having a radiopacity higher than a radiopacity of a material forming other parts of the layer 544, defines a radiographic marker 554. Also indicated in FIG. 9A is an axis $A_P$ that passes through a reference point P described in connection with FIGS. 9B through 9D.

Figure 9B:
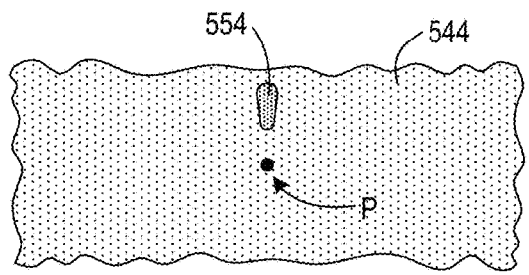
FIG. 9B is a partially schematic view from the location indicated in FIG. 9A.
Figure 9C:
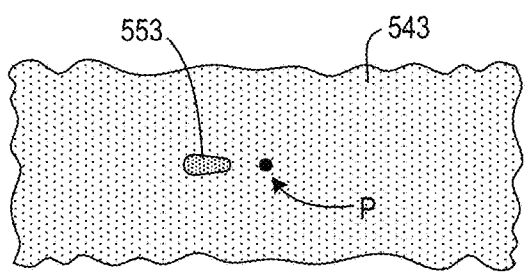
FIGS. 9C, 9D, and 9E are partially schematic area cross-sectional views from the locations indicated in FIG. 9A.
Figure 9D:
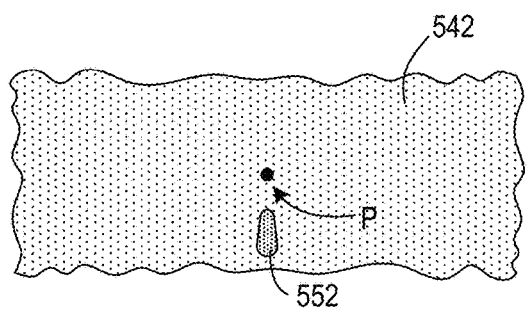
Figure 9E:
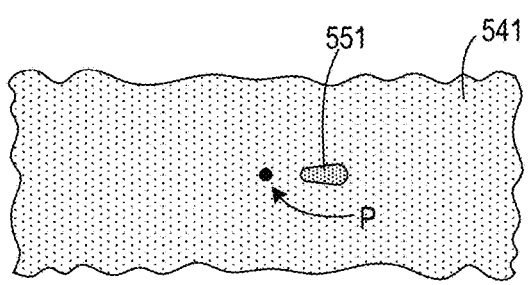
Figure 10A:
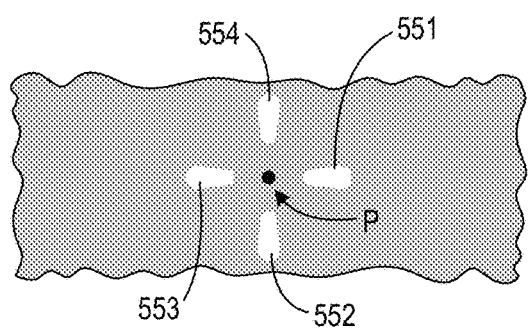
FIGS. 10A, 10B, 10C, and 10D are simulated radiographic images showing the coating of FIG. 9A having different amounts of wear.
Figure 10B:
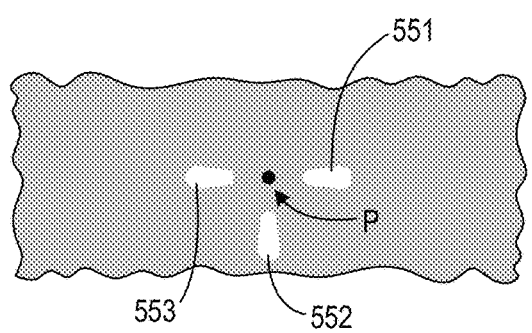
Figure 10C:
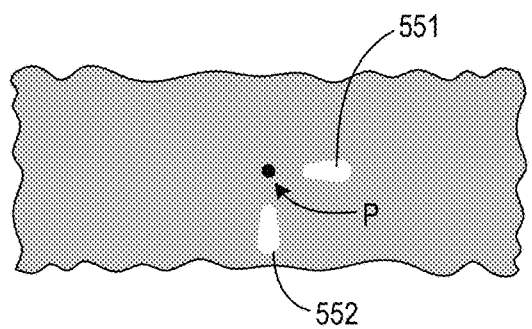
Figure 10D:
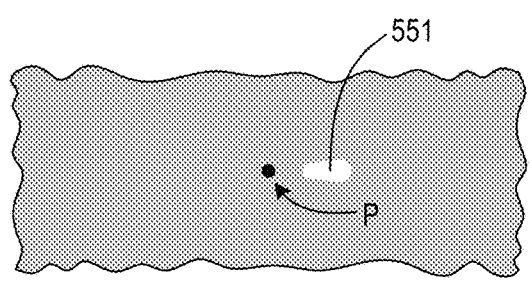

FIG. 9B is a partially schematic view, from the location indicated in FIG. 9A, showing a shape of the radiographic marker 554 and a location of the marker 554, relative to the reference point P, in the layer 544. FIG. 9C is a partially schematic view, from the location indicated in FIG. 9A, showing a shape of the radiographic marker 553 and a location of the marker 553, relative to the reference point P, in the layer 543. FIG. 9D is a partially schematic view, from the location indicated in FIG. 9A, showing a shape of the radiographic marker 552 and a location of the marker 552, relative to the reference point P, in the layer 542. FIG. 9E is a partially schematic view, from the location indicated in FIG. 9A, showing a shape of the radiographic marker 551 and a location of the marker 551, relative to the reference point P, in the layer 541.

FIGS. 10A, 10B, 10C, and 10D are simulated radiographic images showing the coating 540 in different wear conditions. In the simulated radiographic image 531a of FIG. 10A, the coating 540 is fully intact. The markers 551-554 are all present and visible. The presence of the four markers 551-554 indicates that all coating layers are intact. In the simulated radiographic image 531b of FIG. 10B, the layer 544 has worn away. The absence of the marker 554, combined with the presence of the markers 553, 552, and 551, indicates that the layer 544 is no longer present but that the layers 541-543 are present. In the simulated radiographic image 531c of FIG. 10C, the layers 544 and 543 have worn away. The absence of the markers 554 and 553, combined with the presence of the markers 552 and 551, indicates that the layers 544 and 543 are no longer present but that the layers 541 and 542 are present. In the simulated radiographic image 531d of FIG. 10D, the layers 544-542 have worn away. The absence of the markers 554, 553, and 552, combined with the presence of the marker 551, indicates that the layers 544-542 are no longer present but that the layer 541 is present.

As can be appreciated from FIGS. 10A-10D, markers can be arranged in a pattern so that changes in the pattern indicate a degree of wear. Although the example FIGS. 9A-10D shows markers are arranged in a pattern similar to locations on a clock face, other shapes and/or patterns of markers may be used. For example, multiple layers could comprise respective circular markers of different sizes that are arranged concentrically. As but another example, multiple layers could comprise respective line markers that are arranged in a pattern (e.g., end-to-end, parallel) that allows the absence of a line to be readily detected.

Use of mechanical components with radiographic markers may facilitate inspection of a mechanical system without disassembly and/or while that system is operating. Disassembly of a mechanical system may be time-consuming and/or otherwise impractical and/or inconvenient, and may preclude inspection of components while the assembled system is operating. Moreover, disassembly may disturb a configuration of components that may be part of a problem (e.g., misaligned or improperly installed components) that an inspection is trying to diagnose. Materials may be selected for mechanical system components and/or for coatings so as to increase contrast of markers relative to system components in radiographic images. For example, a housing material may be selected to have a lower radiopacity than system components that may be subject to inspection. Even if design requirements may necessitate fabricating a housing or system components from high radiopacity materials, however, components of a prototype system may be fabricated from materials having much lower radiopacities so as to allow radiographic inspection (using radiographic markers) during prototype testing and/or evaluation.

One or more physical elements (and/or portion(s) thereof) and/or methods (and/or portions thereof) described herein may be used in combination with one or more physical elements (and/or portion(s) thereof) and/or methods (and/or portions thereof) described in the U.S. patent application Ser. No. 17/402,339, titled "Flexible and/or Deformable Mechanical Elements With Radiographic Markers" and filed on Aug. 13, 2021. Said application, in its entirety, is incorporated by reference herein.

For the avoidance of doubt, the present application includes, but is not limited to, the subject-matter described in the following numbered clauses:

1. An apparatus comprising a first component comprising a first solid body formed from a first parent material, the first component further comprising one or more radiographic markers forming at least a portion of a first interface surface of the first component.
2. The apparatus of clause 1, wherein the one or more radiographic markers comprise one or more marker materials having one or more radiopacities greater that a radiopacity of the first parent material.
3. The apparatus of clause 1 or clause 2, wherein the one or more radiographic markers are in a pattern that comprises variation in at least one of: presence of the one or more marker materials, thickness of the one or more marker materials, or composition of the one or more marker materials.
4. The apparatus of any of clauses 1-3, further comprising a second component comprising a second solid body and a second interface surface, wherein the first component is movably coupled to the second component, and wherein the first component and the second component are configured for contacting relative motion of the first interface surface and the second interface surface.
5. The apparatus of any of clause 4, wherein the second component comprises a housing containing at least a portion of the first component comprising the first interface surface.
6. The apparatus of 4, further comprising a housing, containing the first component and the second component, that is opaque to visible light.
7. The apparatus of any of clauses 4-6, wherein the contacting relative motion of the first interface surface and the second interface surface comprises a sliding motion of the second interface surface relative to the first interface surface and/or a rolling motion of the first interface surface and the second interface surface.
8. The apparatus of any of clause 4-7, wherein: the first component comprises a gear; the first component comprises a cam and the second component comprises a cam follower; the first component comprises a cam follower and the second component comprises a cam; the first component comprises one of a ring or a piston and the second component comprises a cylinder; the first component comprises a cylinder and the second component comprises one of a ring or a piston; first component comprises a journal and the second component comprises a journal bearing; first component comprises a journal bearing and the second component comprises a journal; the first component comprises a screw and the second component comprises a component with internal threads engaging threads of the screw; the first component comprises a component with internal threads engaging threads of a screw and the second component comprises the screw; the first component comprises a bearing and the second component comprises a bearing race; the first component comprises a bearing race and the second component comprises a bearing; the first component comprises a wheel and the second component comprises a surface contacting a surface of the wheel; or the first component comprises a surface contacting a surface of a wheel the second component comprises the wheel.

9. The apparatus of any of clauses 4-8, further comprising: a second radiographic marker forming at least a portion of the second interface surface, wherein the second radiographic marker comprises a marker material having a radiopacity greater than a radiopacity of a second parent material forming the second solid body.

10. The apparatus of any of clauses 1-9, wherein: the one or more marker materials comprise a first marker material and a second marker material, the first marker material has a radiopacity greater than a radiopacity of the second marker material, and/or the second marker material is located between the first marker material and the first parent material.

11. The apparatus of clause 10, wherein the first marker material is comprised by a first layer and the second marker material is comprised by a second layer, and/or wherein the second marker material has a radiopacity greater than the radiopacity of the first parent material.

12. The apparatus of any of clauses 1-11, wherein the one or more radiographic markers are in a pattern that comprises one or more indicia.

13. The apparatus of any of clauses 1-12, wherein the one or more radiographic markers are in a pattern configured to indicate, in a radiographic image of a portion of the apparatus comprising the first interface surface, at least one of: wear of the first interface surface, damage to the first interface surface, or an orientation of the first interface surface.

14. The apparatus of any of clauses 1-13, wherein the one or more radiographic markers are in a pattern that comprises a plurality of radiographic markers contained in respective layers.

15. The apparatus of any of clauses 1-14, wherein the one or more radiographic markers comprise one or more coatings forming at least a portion of the first interface surface.

16. A method comprising positioning at least a portion of an apparatus according to any of clauses 1-15 between a radiographic emitter and a radiographic sensor.

17. The method of clause 16, further comprising generating, based on detection by the sensor of radiographic energy emitted from the radiographic emitter, one or more radiographic images comprising a representation of the at least a portion of the first interface surface.

18. The method of clause 17, wherein the generating comprises generating the one or more radiographic images by emitting the radiographic energy while the apparatus is operating.

The foregoing has been presented for purposes of example. The foregoing is not intended to be exhaustive or to limit features to the precise form disclosed. The examples discussed herein were chosen and described in order to explain principles and the nature of various examples and their practical application to enable one skilled in the art to use these and other implementations with various modifications as are suited to the particular use contemplated. The scope of this disclosure encompasses, but is not limited to, any and all combinations, subcombinations, and permutations of structure, operations, and/or other features described herein and in the accompanying drawing figures.

The invention claimed is:

1. An apparatus comprising:
   a first component comprising a first solid body formed from a first parent material, the first component further comprising a pattern of one or more radiographic markers forming at least a portion of a first interface surface of the first component, wherein:
   the one or more radiographic markers comprise one or more marker materials having one or more radiopacities greater that a radiopacity of the first parent material, and
   the pattern comprises variation in at least one of: presence of the one or more marker materials, thickness of the one or more marker materials, or composition of the one or more marker materials; and
   a second component comprising a second solid body and a second interface surface, wherein the first component is movably coupled to the second component, and wherein the first component and the second component are configured for contacting relative motion of the first interface surface and the second interface surface.

2. The apparatus of claim 1, wherein the second component comprises a housing containing at least a portion of the first component comprising the first interface surface.

3. The apparatus of claim 1, further comprising a housing, containing the first component and the second component, that is opaque to visible light.

4. The apparatus of claim 1, wherein the pattern comprises a pattern configured to indicate, in a radiographic image of a portion of the apparatus comprising the first interface surface, at least one of:
   wear of the first interface surface,
   damage to the first interface surface, or
   an orientation of the first interface surface.

5. The apparatus of claim 1, wherein the contacting relative motion of the first interface surface and the second interface surface comprises a sliding motion of the second interface surface relative to the first interface surface.

6. The apparatus of claim 5, wherein:
   the first component comprises a gear;
   the first component comprises a cam and the second component comprises a cam follower;
   the first component comprises a cam follower and the second component comprises a cam;
   the first component comprises one of a ring or a piston and the second component comprises a cylinder;
   the first component comprises a cylinder and the second component comprises one of a ring or a piston;
   first component comprises a journal and the second component comprises a journal bearing;
   first component comprises a journal bearing and the second component comprises a journal;
   the first component comprises a screw and the second component comprises a component with internal threads engaging threads of the screw; or the first component comprises a component with internal threads engaging threads of a screw and the second component comprises the screw.

7. The apparatus of claim 1, wherein the contacting relative motion of the first interface surface and the second interface surface comprises a rolling motion of the first interface surface relative to the second interface surface.

8. The apparatus of claim 7, wherein:
the first component comprises a bearing and the second component comprises a bearing race;
the first component comprises a bearing race and the second component comprises a bearing;
the first component comprises a wheel and the second component comprises a surface contacting a surface of the wheel; or
the first component comprises a surface contacting a surface of a wheel and the second component comprises the wheel.

9. The apparatus of claim 1, further comprising:
a second radiographic marker forming at least a portion of the second interface surface, wherein the second radiographic marker comprises a marker material having a radiopacity greater than a radiopacity of a second parent material forming the second solid body.

10. The apparatus of claim 1, wherein:
the one or more marker materials comprise a first marker material and a second marker material,
the first marker material has a radiopacity greater than a radiopacity of the second marker material, and
the second marker material is located between the first marker material and the first parent material.

11. The apparatus of claim 1, wherein the pattern comprises one or more indicia.

12. A method comprising:
positioning at least a portion of a mechanical system between a radiographic emitter and a radiographic sensor, wherein:
the mechanical system comprises a first component comprising a first solid body formed from a first parent material, the first component further comprising one or more radiographic markers forming at least a portion of a first interface surface of the first component,
the one or more radiographic markers comprise one or more marker materials having one or more radiopacities greater that a radiopacity of the first parent material,
the mechanical system further comprises a second component comprising a second solid body and a second interface surface, wherein the first component is movably coupled to the second component, and wherein the first component and the second component are configured for contacting relative motion of the first interface surface and the second interface surface, and
the at least the portion of the mechanical system comprises the at least the portion of the first interface surface; and
generating, based on detection by the sensor of radiographic energy emitted from the radiographic emitter, one or more radiographic images comprising a representation of the at least the portion of the first interface surface.

13. The method of claim 12, wherein the generating comprises generating the one or more radiographic images by emitting the radiographic energy while the mechanical system is operating.

14. The method of claim 12, wherein the one or more radiographic markers comprise a pattern of the one or more radiographic markers, and wherein the pattern comprises variation in at least one of: presence of the one or more marker materials, thickness of the one or more marker materials, or composition of the one or more marker materials.

15. The method of claim 12, wherein the mechanical system further comprises a housing, containing the first component and the second component, that is opaque to visible light.

16. The method of claim 12, wherein the contacting relative motion of the first interface surface and the second interface surface comprises a sliding motion of the second interface surface relative to the first interface surface or a rolling motion of the second interface surface relative to the first interface surface.

17. The method of claim 12, wherein:
the one or more marker materials comprise a first marker material and a second marker material,
the first marker material has a radiopacity greater than a radiopacity of the second marker material, and
the second marker material is located between the first marker material and the first parent material.

18. An apparatus comprising:
a first component comprising a first solid body formed from a first parent material, the first component further comprising one or more radiographic markers forming at least a portion of a first interface surface of the first component, wherein:
a radiographic marker of the one or more radiographic markers comprise a plurality of layers,
a first layer of the plurality of layers comprises a first marker material having a radiopacity greater than a radiopacity of the first parent material,
a second layer of the plurality of layers comprises a second marker material having a radiopacity greater than the radiopacity of the first parent material and less than the radiopacity of the first marker material, and
the second layer is located between the first parent material and the first layer; and
a second component comprising a second solid body and a second interface surface, wherein the first component is movably coupled to the second component, and wherein the first component and the second component are configured for contacting relative motion of the first interface surface and the second interface surface.

19. The apparatus of claim 18, further comprising a housing, containing the first component and the second component, that is opaque to visible light.

20. The apparatus of claim 18, further comprising:
a second radiographic marker forming at least a portion of the second interface surface, wherein the second radiographic marker comprises a marker material having a radiopacity greater than a radiopacity of a second parent material forming the second solid body.

* * * * *